United States Patent [19]

Monnier et al.

[11] Patent Number: 5,214,138

[45] Date of Patent: May 25, 1993

[54] IMIDAZOPYRIDINIUM COMPOUND AND PROCESSES FOR ISOLATING, IDENTIFYING, AND CHEMICALLY SYNTHESIZING SAME

[75] Inventors: Vincent M. Monnier, Shaker Hts.; David R. Sell, Cleveland Hts., both of Ohio

[73] Assignee: Case Western Reserve University, Cleveland, Ohio

[21] Appl. No.: 453,959

[22] Filed: Dec. 20, 1989

[51] Int. Cl.$^5$ .............. A61K 31/70; A61K 31/44; C07H 17/02; C07H 19/04
[52] U.S. Cl. .............. 536/17.3; 536/27.13; 530/356; 530/840
[58] Field of Search .............. 536/17.3, 23, 17.3, 536/23, 24; 514/267, 367, 45, 79; 546/121; 424/256, 263; 435/29; 530/356, 840

[56] References Cited

U.S. PATENT DOCUMENTS

| | | | |
|---|---|---|---|
| 3,985,891 | 10/1976 | Kutter et al. | 424/263 |
| 4,096,264 | 6/1978 | Bochis et al. | 424/256 |
| 4,672,031 | 6/1987 | Prockop | 435/29 |
| 4,780,452 | 10/1988 | Krenitsky et al. | 514/45 |
| 4,782,142 | 11/1988 | Bardos et al. | 536/23 |
| 4,894,441 | 1/1990 | Menicagli | 530/356 |

*Primary Examiner*—Ronald W. Griffin
*Assistant Examiner*—Louise N. Leary
*Attorney, Agent, or Firm*—Fay, Sharpe, Beall, Fagan, Minnich & McKee

[57] ABSTRACT

The present invention is directed to a novel imidazo [4,5b] pyridinium molecule composed of a lysine and an arginine residue crosslinked with a pentose sugar. The novel imidazo [4,5b] pyridinium compound, referred to as "pentosidine", was isolated from proteineous tissue undergoing advanced glycosylation and is believed to be one of the principal products involved in the non-enzymatic browning and/or aging of proteins. Assaying for the pentosidine molecule makes it possible to assess the degree of aging of proteins in vivo as mediated by pentose induced crosslinking and modulated by disease such as diabetes and nephropathy In addition, the pentosidine molecule may be utilized through the production of monoclonal antibodies thereto and/or the preparation of test kits, etc. for diagnostic, as well as therapeutic purposes (i.e. development of agents which inhibit the non-enzymatic browning reaction, etc.).

13 Claims, 13 Drawing Sheets

IMIDAZOPYRIDINIUM COMPOUND AND PROCESSES FOR ISOLATING, IDENTIFYING, AND CHEMICALLY SYNTHESIZING SAME

BACKGROUND OF THE INVENTION

The present invention relates to a process for isolating and identifying a novel imidazo [4,5b] pyridinium molecule, referred to by the inventors as "pentosidine", from the extracellular matrix of humans and other mammals. The recently isolated imidazo [4,5b] pyridinium molecule, or pentosidine, is believed to be produced according to the non-enzymatic reaction of sugars with various amino acid or protein residues during the aging and/or degradation of proteins. In this regard, the pentosidine the molecule has been structurally characterized to consist essentially of a lysine and an arginine residue crosslinked by a pentose. Furthermore, the novel imidazo [4,5b] pyridinium or pentosidine molecule of the invention has been chemically synthesized in order to confirm the structural arrangement of the isolated molecule. The present invention is further directed to the use of the recently isolated, characterized, and chemically synthesized pentosidine molecule in various processes and/or compositions for studying the aging and/or degradation of proteins in humans and other mammals.

The extracellular matrix of humans and other mammals undergoes progressive changes during aging that are characterized by decreased solubility (Schnider, S. L., and Kohn, R. R., *J. Clin. Invest.* 67, pp. 1630–1635, 1981), decreased proteolytic digestibility (Hamlin, C. R., Luschin, J. H., and Kohn, R. R., *Exp. Gerontol.* 13, pp. 415–523, 1978), increased heat denaturation time (Snowden, J. M., Eyre, D. R., and Swann, D. H., *Biochem. Biophys. Acta.* 706, pp. 153–157, 1982) and accumulation of yellow and fluorescent material (LaBella, F. S., and Paul, G., *J. Gerontol.* 20, pp. 54–59, 1964). These changes, which affect particularly collagen-rich tissues and appear to be accelerated in diabetes, are thought to result from the formation of age-related intermolecular crosslinks.

Elucidation of the structure of these age-related intermolecular crosslinks has been for many years of major interest to gerontologists and collagen chemists for two principal reasons. First, there appears to exist an inverse relationship between mammalian longevity and aging rate of collagen (Kohn, R. R. in *Testing the Theories of Aging* (Adelman, R. C., and Roth, G. S., eds.) pp. 221–231, CRC Press, Inc., Boca Raton, Fla.) suggesting that the process which governs longevity may express itself at least partially in the aging rate of collagen. Second, the progressive increase in stiffness of collagen-rich tissues like arteries, lungs, joints and the extracellular matrix has been associated with age-related diseases such as hypertension, emphysema, decreased joint mobility and ability to fight infections. Thus, elucidation of the nature of extracellular matrix crosslinking in aging is of both practical and theoretical interest.

Along these lines, the present inventors and others previously postulated that the advanced Maillard or nonenzymatic glycosylation reaction which occurs between reducing sugars, e.g., glucose, and amino groups on proteins could explain some of the age and diabetes-related changes that affect long-lived proteins through browning and crosslinking (Monnier, V. M., and Cerami, A., *Science*, 211, pp. 491–493, 1981). However, direct demonstration of this hypothesis has not been possible since the structures of Maillard protein adducts and crosslinks were previously unknown.

In this regard, Cerami, et al., U.S. Pat. Nos. 4,665,192 and 4,758,583 reported the discovery of a new and useful fluorescent chromophore -2-(2-furoyl)-4(5)-2(furanyl)-1H-imidazole (FFI) and a method of utilizing this chromophore for inhibiting protein aging. However, the present inventors have demonstrated that the FFI compound described in these patents is merely an artifact of acid hydrolysis and alkalization with ammonia and is not one of the end products of extended non-enzymatic polypeptide glycosylation (Njoroge, et al., *J. Biol. Chem.*, 263: 10646–10652, 1988).

However, notwithstanding the above, recent observations continue to suggest that some of the changes occurring in the aging process of collagen could be explained by the Maillard or non-enzymatic browning reaction which occurs in stored or heated foodstuffs (Monnier, V. M. and Cerami, A., *Am. Chem. Soc.* 215, 431, 1983). In this regard, reducing sugars react non-enzymatically with the free amino groups of the proteins to form insoluble, highly crosslinked, yellow and fluorescent products. Studies on the potential occurrence of the non-enzymatic browning reaction in vivo demonstrated an age-related increase in dura and skin collagen-linked fluorescence at 440 nm (excitation at 370 nm) and chromophores absorbing above 300 nm (Monnier, V. M., Kohn, R. R., and Cerami, A., *Proc. Natl. Acad. Sci.* 81, 583, 1984) (Monnier, V. M., Vishwanath, V., Frank, K. E., Elmets, C. A., Dauchot, P., and Kohn, R. R., *New Engl. J. Med.* 314, 403, 1986). Similar spectroscopical changes could be duplicated by incubating collagen with reducing sugars such as glucose, glucose-6-phosphate or ribose (Monnier, V. M., Kohn, R. R., and Cerami, A., *Proc. Natl. Acad. Sci.* 81, 583, 1984) (Kohn, R. R., Cerami, A., Monnier, V. M., *Diabetes* 33, 57, 1984). In addition, it was demonstrated that collagen incubated with these sugars was highly crosslinked suggesting that the sugar-derived fluorophores-chromophores could act as intra- or intermolecular crosslinks (Monnier, V. M., Kohn, R. R., and Cerami, A., *Proc. Natl. Acad. Sci.* 81, 583, 1984) (Kohn, R. R., Cerami, A., Monnier, V. M., *Diabetes* 33, 57, 1984).

The potential role of the Maillard reaction in these changes was further substantiated by the observation that non-enzymatic glycosylation which initiates the Maillard reaction was increased in diabetic and aging collagen and by observations in subject with Type I (insulin-dependent) diabetes that revealed a dramatic increase in collagen-linked fluorescence (Monnier, V. M., Vishwanath, V., Frank, K. E., Elmets, C. A., Dauchot, P., and Kohn, R. R., New Engl. J. Med. 314, 403, 1986) (Vishwanath, V., Frank, K. E., Elmets, C. A., Dauchot, P. J., Monnier, V. M., Diabetes 35, 916, 1986).

Although age-related acceleration of collagen browning may be explained by the Maillard reaction, the evidence presented for support of this hypothesis has been very circumstantial. More particularly, such evidence is based on spectroscopical changes of collagen with aging and diabetes in vivo with conspicuous similarities produced by the incubation of young collagen with reducing sugars in vitro. Because of uncertainty in the exact nature of the fluorescence produced during the aging of proteins, as well as the particular nature of the protein adducts and crosslinks involved therein, the present inventors initiated a study that resulted in the present invention with the ultimate aim of elucidating the nature of the collagen-linked fluorescence which increases in aging and diabetes.

In this regard, the present inventors conducted a systematic investigation of the chemical nature of the fluorescence that accumulates in aging human collagen. Two novel fluorophores, nicknamed "P" and "M", with excitation/emission maxima at 335/385 nm and 360/460 nm, respectively, were isolated from insoluble collagen following proteolytic digestion and chromatography (Sell, D. R., and Monnier, V. M., Conn. Tiss. Res. 19, pp. 77–92, 1989). An age-related effect was noted for both types of fluorophores (i.e. the presence of the fluorophores increased with age). Although fluorophore M was borohydride reducible and unstable to acid hydrolysis, thereby suggesting that M had an iminopropene-type configuration which substantiated, but did not prove, that glucose was responsible for its origin, the fluorescence properties of the 335/385 fluorophore, i.e. fluorophore "P", were found unchanged following acid hydrolysis in 6 N HCl for 24 hours at 110° C. As a result of its resistance to acid hydrolysis, a larger quantity of fluorophore P was purified from acid hydrolyzed dura matter collagen and its structure was elucidated using $^1$H-NMR, $^{13}$C-NMR and MS/MS fast atom bombardment spectroscopy. Structure elucidation of fluorophore "P" led to the discovery of a pentose-mediated protein crosslink named "pentosidine".

SUMMARY OF THE INVENTION

In one aspect, the present invention is directed to a novel imidazo [4,5b] pyridinium molecule composed of a lysine and an arginine residue crosslinked with a pentose sugar. The novel imidazo [4,5b] pyridinium compound, referred to as "pentosidine", was isolated from proteineous tissue undergoing advanced glycosylation and is believed to be one of the principal products involved in the non-enzymatic browning and/or aging of proteins. Assaying for the pentosidine molecule makes it possible to assess the degree of non-enzymatic glycosylation occurring. In addition, the pentosidine molecule may be utilized through the production of monoclonal antibodies thereto and/or the preparation of test kits, etc. for diagnostic, as well as therapeutic purposes (i.e. development of agents which inhibit the non-enzymatic browning reaction, etc.).

Structural elucidation of the pentosidine molecule indicates that its precise chemical name 3-H-imidazol [4,5b] pyridine-4-hexanoic acid, alpha amino-2 [(4-amino-4-carboxybutyl) amino), and that its structural composition is as follows:

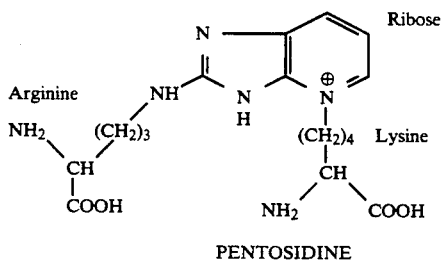

PENTOSIDINE

In a further aspect, the present invention is directed to a process for chemically synthesizing the pentosidine molecule. The structure of the isolated pentosidine molecule was confirmed by the non-enzymatic reaction of ribose with lysine and arginine residues.

In additional aspect, the present invention is directed to a process for isolating the pentosidine molecule from insoluble collagen tissue through the acid-hydrolysis of insoluble collagen and the structural elucidation of the isolated molecule using $^1$H-NMR, $^{13}$C-NMR and various other spectroscopy techniques.

Other aspects and advantages of the present invention will become apparent to those skilled in the art upon a review of the following materials.

BRIEF DESCRIPTION OF THE DRAWINGS

The following is a brief description of the drawings which are presented for the purposes of illustrating the invention and not for the purposes of limiting same.

DETAILED DESCRIPTION OF THE INVENTION

Figures 1A, 1B, 1C:
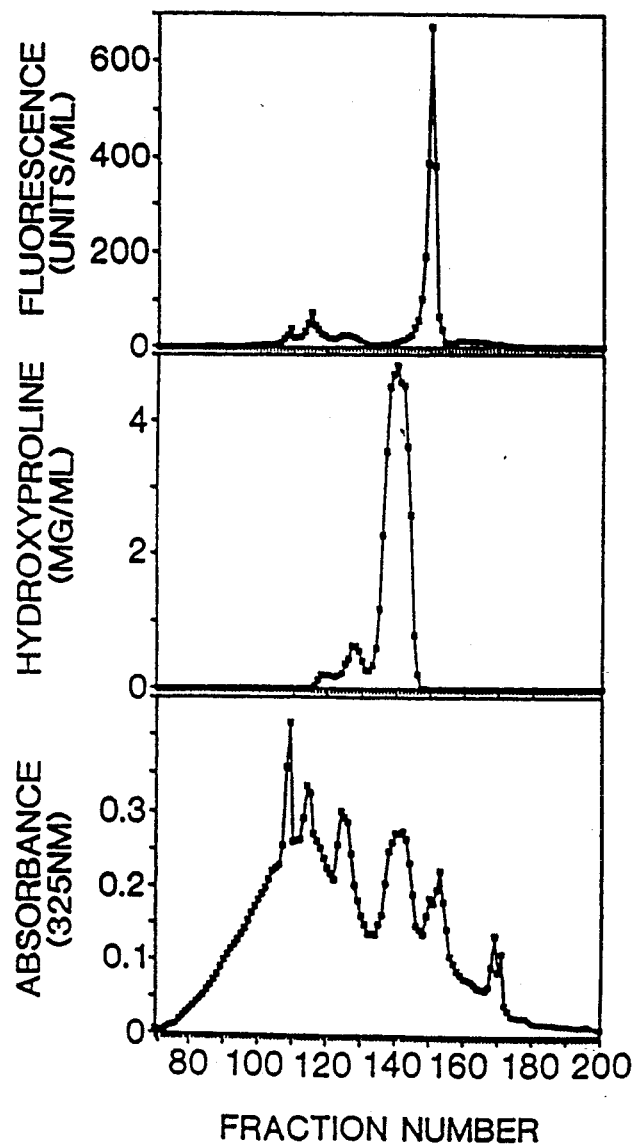
FIGS. 1A–1C are graphs illustrating the results [i.e. fluorescence (FIG. 1A), hydroxyproline (FIG. 1B), and absorbance (FIG. 1C)], produced by the fractions obtained by gel filtration on Bio-Gel P-2 of acid-hydrolyzed human dura matter. Fluorescence was monitored at excitation/emission wavelengths of 335/385 nm.
Figure 2A:
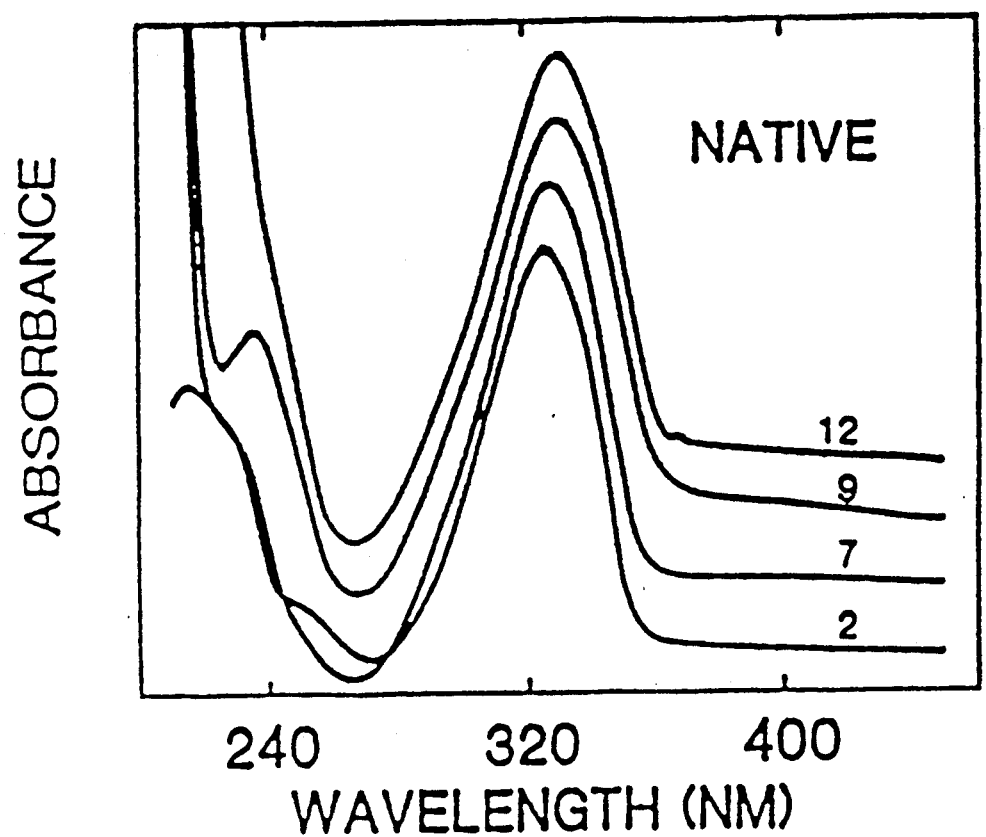
FIGS. 2A, 2B, 2C and 2D are graphs illustrating the absorption (FIGS. 2A and 2B) and fluorescence-excitation (FIGS. 2C and 2D) spectra at pH 2, 7, 9, and 12 of fluorophore P (pentosidine) isolated from native human dura mater (FIGS. 2A and 2C) and a synthetic incubation system of heating lysine, arginine, and ribose together at 80° C. for one hour (FIGS. 2B and 2D). Fluorescence-excitation spectra were monitored as follows: for the emission spectra on the right, excitation was at 335 nm, and for the excitation spectra on the left, emission was at 385 nm.
Figure 2B:
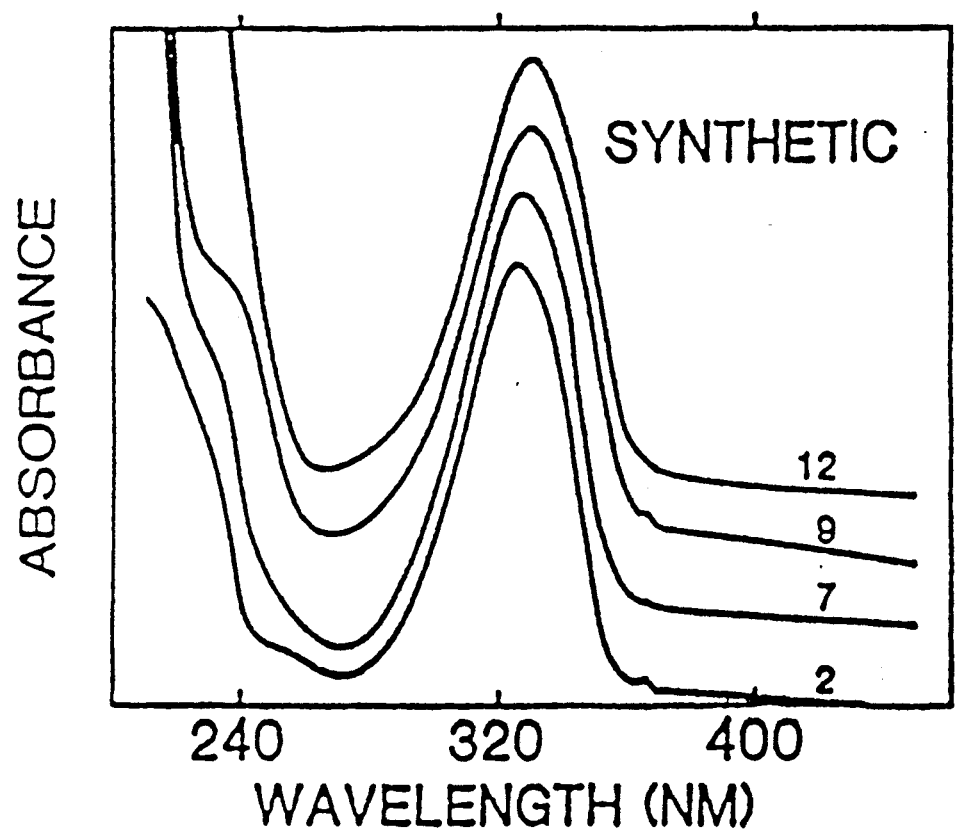
Figure 2C:
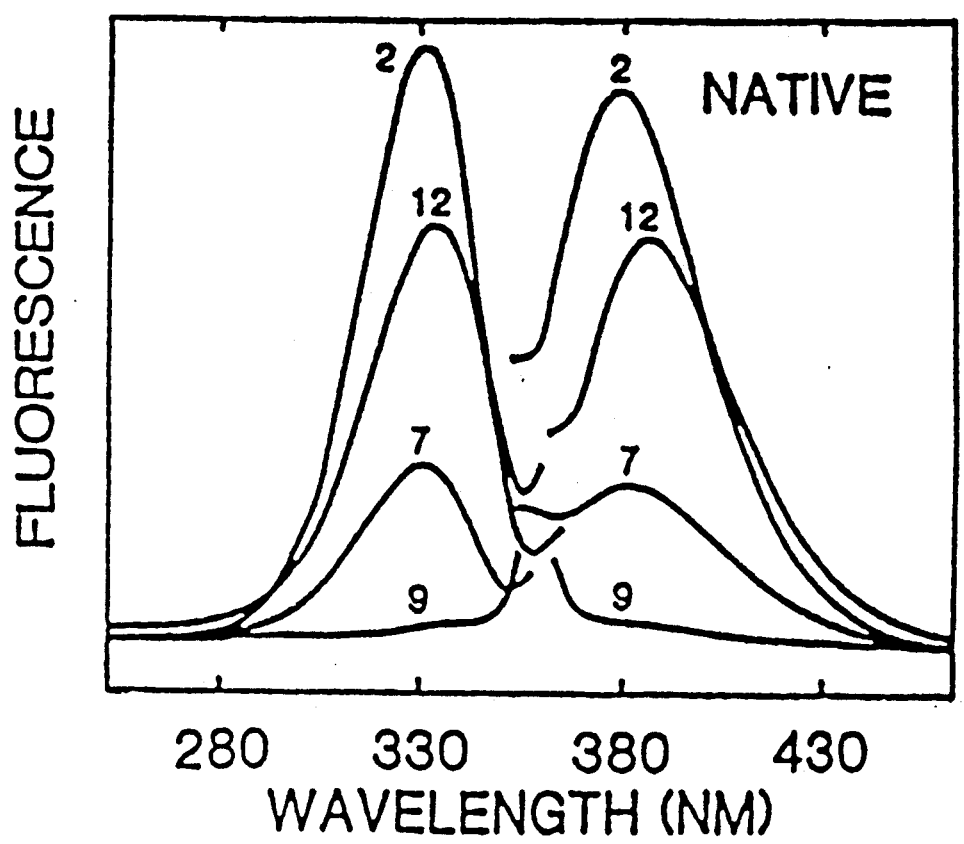
Figure 2D:
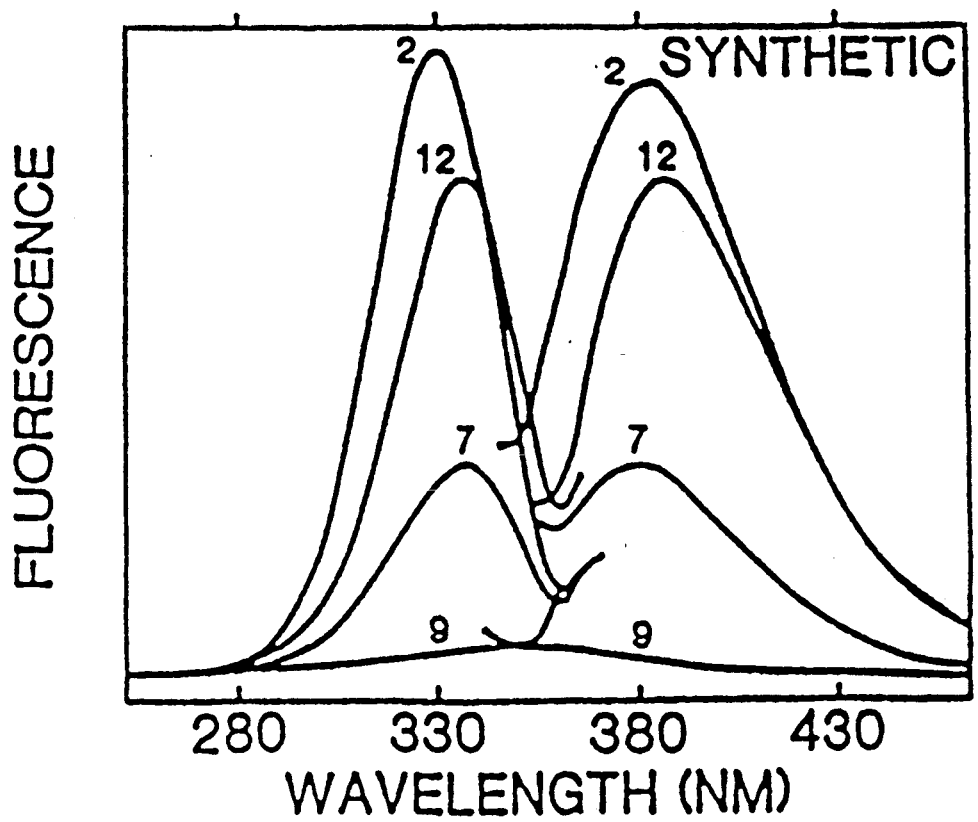

The present invention is directed to the isolation and identification of an acid resistant fluorescent molecule from the extracellular matrix of humans and other mammals. Structure elucidation of the isolated fluorescent molecule revealed the presence of an imidazo [4,5b] pyridinium molecule comprising a lysine and an arginine residue crosslinked by a pentose. Confirmation of this structural arrangement was achieved in vitro by the non-enzymatic reaction of ribose with lysine and arginine residues.

In addition, it has been determined that the newly discovered crosslink, named "pentosidine" by the inventors, can also be synthesized with isomers of ribose, arabinose, xylose, and lyxose, as well as by incubating young human collagen with these sugars at 37° C. Moreover, pentosidine was found in a variety of human tissues including plasma proteins and red blood cells. Its presence in cells grown in culture strongly suggests ribose or ribonucleotide metabolites as precursors. The unexpected discovery of pentose-mediated protein crosslinking, as well as the pentosidine crosslink, provides useful tools for the further investigation and explanation of the aging process.

More particularly, the present invention relates to the use of a novel fluorophore compound (formerly referred to as "flurophore P" and now referred to as "pentosidine") which has been isolated from human collagen undergoing advanced non-enzymatic glycosylation and identified as 3-H-imidazol [4,5b] pyridine-4-hexanoic acid, alpha amino-2[(4-amino-4-carboxybutyl) amino]. The imidazopyridinium compound is believed to be one of the end products of the extended non-enzymatic polypeptide glycosylation reaction normally associated with the structural and functional changes in tissues that occur during the aging process, and has also been observed to occur at an accelerated rate in individuals suffering from diabetes. By identifying the occurrence of advanced glycosylation through the detection of the specified fluorophore compound of the present invention, the degree of cellular stress or injury caused by diabetes, aging, and/or uremia may be determined. In addition, detection of the pentosidine compound may also aid in determining who among diabetic subjects is at risk of developing diabetic complications. Thus, the newly discovered fluorescent imidazopyridinium compound, or pentosidine, as well as antibodies specific to said compound, may be used in connection with various diagnostic techniques, to determine the advancement of glycosylation in protein specimens.

Furthermore, since it is generally thought that the aging effects produced by the non-enzymatic polypeptide glycosylation of the significant protein masses of the body (such as collagen, elastin, lens protein, nerve proteins, and the kidney glomerular basement membranes) is caused by the cross-linking of sugars with the amino acids of the proteins, the imidazopyridinium compound of the present invention (i.e. pentosidine) may also be utilized as an exploratory tool for the development and testing of possible agents capable of interfering with the cross-linking process, thereby inhibiting protein aging. Hence, the present invention may reduce the incidence of pathologies involving the cross linking of proteins such as atherosclerosis, osteoarthritis, loss of elasticity and wrinkling of the skin, and stiffening of joints.

The present inventors have developed a process for isolating and purifying a 2-alkyl amino-4-alkyl imidazopyridinium compound (specifically, 3-H-imidizol [4,5b] pyridine-4-hexanoic acid, alpha amino-2[(4-amino-4-carboxybutyl) amino] , i.e. "pentosidine"), a newly discovered imidazopyridinium compound representing a cross link between the amino acids lysine and arginine, from a pool of insoluble human dura mater collagen following enzymatic hydrolysis and sequential purification steps utilizing Sephadex G50, paper, cation, and high performance liquid chromatography (the specific procedures and material involved in this process are more clearly set forth below in the examples). The imidazopyridinium compound was detected on the basis of its fluorescence at 385 nm upon excitation at 335 nm. Its maximum UV was at 325 nm.

Furthermore, since the compound was not destroyed by acid hydrolysis, this allowed it to be directly prepared from batch quantities of collagen. More particularly, because the pentosidine molecule was resistant to acid hydrolysis, a larger quantity of the molecule could be purified from acid hydrolyzed dura mater collagen. The compound may then be assayed by HPLC with a fluorescence detector. Structure elucidation of the fluorescent compound by $^1$H-NMR, COSY, $^{13}$C-NMR, MS/MS FAB Spectroscopy indicated the presence of an imidazopyridinium compound involving lysine and arginine and a 5-carbon moiety in the heterocyclic ring.

Moreover, in a study involving skin specimens obtained at autopsy, the imidazopyridinium compound was found to increase exponentially with age. High levels were detected in diabetic subjects with nephropathy as well as in uremic subjects without nephropathy.

In addition, the inventors have chemically synthesized their imidazopyridinium compound by the following procedure.

A mixture consisting of 0.1 M D-ribose, L-lysine HCl and L-arginine at pH 7.4 was heated to 80° C. for 60 minutes and passed over Dowex 50×4 resin (H+-form). The resin was washed with one liter H$_2$O, 1 M pyridine with 1L of 2N NaOH. After neutralization and evaporation the concentrate was chromatographed over Bio-Gel P-2 equilibrated in 0.02 M Hepes. Fractions containing the fluorophore were further purified by HPLC using a C-18 reverse phase column and a linear gradient of acetonitrile with 0.01M of heptafluorobutyric acid (HFBA) as counterion. All fluorescence, UV, NMR, and mass spectroscopical properties of the synthetic compound were rigorously identical with those of the native compound. Yield was 0.1% under non-optimized reaction conditions.

The possibility of producing the imidazo-pyridinium compound with pentoses came to the inventors as a big surprise. In this regard, the use of pentoses (i.e. ribose, arabinose, and xylose) in the total synthesis of pentosidine or any imidazopyridinium compound derived from the general reaction:

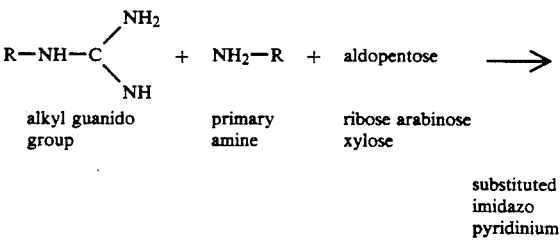

whereby R = aliphatic or aromatic rest.

is completely new. As more particularly discussed below, the in vitro synthesis of pentosidine and/or other imidazopyridine compounds is a valuable tool for researching the aging process.

The specific procedures and materials used in the isolation, characterization, and chemical synthesis of the pentosidine compound of the present invention are set forth below in the following illustration examples.

EXAMPLE 1

Methods and Procedures

Preparation of Pentosidine from Dura Mater

The starting material consisted of insoluble human dura mater (60 g. wet weight) determined to contain greater than 95% collagen on the basis of hydroxyproline content. Hydroxyproline was quantitated as described in Hamlin, et al. (i.e. Hamlin, C. R., Luschin, J. H., and Kohn, R. R., *Exp. Gerontol.* 13, pp. 415–523, 1978) and assumed to make up 14% of the collagen by weight (Hamlin, C. R., and Kohn, R. R., *Biochem. Biophys. Acta*, 236, pp. 458–467, 1971). The dura mater was homogenized twice in phosphate-buffered saline (PBS, pH 7.4), extracted for 24 hours in 2:1 chloroform/methanol, and acid-hydrolyzed under reflux and nitrogen for 36 hours in 6 liters of 6 N HCl. The acid was evaporated at 40° C. The residue was dissolved in water and pH adjusted to 7.4 (NaOH). The material was applied to a 5×150 cm column of Bio-Gel P-2 fine (Bio-Rad Laboratories, Rockville Centre, N.Y.) equilibrated with 0.02 M Hepes (pH 7.4) containing 0.15 M NaCl. Fifteen milliliter fractions were collected at a flow rate of 1 ml/min. Fractions containing the 335/385 fluorophore were pooled, adjusted to pH 8.5 with NaOH and rotary evaporated. The fluorophore was extracted with methanol to remove some of the salts. The methanol, in turn, was evaporated and the residue dissolved in 10 ml of water and acidified with concentrated HCl. Purification was achieved by multiple injections/peak collections using reverse-phase C-18 HPLC and a water/acetonitrile solvent containing consecutively trifluoroacetic acid (TFA), n-heptafluorobutyric acid (HFBA), and again TFA as counterions. The final product was judged pure by virtue of a single ninhydrin positive spot on paper chromatography and a single UV and fluorescent HPLC peak under various chromatographic conditions using a reverse-phase column.

Synthesis and Purification of Pentosidine from a Synthetic System

Three liters containing 100 mM each of L-arginine, L-lysine and D-ribose, at pH 7.3, Were heated for 1 hr at 80° C. The cooled mixture was poured onto a Buchner funnel filled with Dowex 50×4−400 ion-exchange resin (Aldrich Chem. Co., Inc., Milwaukee, Wisc.) equilibrated according to conditions of Boas (Boas, N. F., *J. Biol. Chem.*, 204, pp. 553–563, 1953). The resin was washed with 2 liters each of water and 1 M pyridine, followed by elution of pentosidine-containing material with 1 liter of 2 N NaOH. The material was then adjusted to pH 7.4 with HCl, concentrated by rotary evaporation, passed through a Bio-Gel P-2 column and purified by HPLC as described above. The material was also chromatographed on Whatman 17 Chr paper (Whatman Inc., Clifton, N.J.) using 1:1 water/pyridine. Upon elution from the paper, the material was reinjected and collected by reversed-phase HPLC using TFA as the counterion.

High Performance Liquid Chromatography (HPLC)

A Waters HPLC (Waters Chrom. Div., Milford, Mass.) with Model 510 pumps, U6K injector, and a 680 controller was used. The effluent was monitored at 385 nm (excitation at 335 nm) with a J4–8202 Aminco-Bowman spectrophotofluorometer (SLM Instru., Inc., Urbana, Ill. equipped with a 9 μl continuous flow cell. Separations were made on either a 4.6 mm (analytical) or 1.0 cm (semi-preparative) ×25 cm Vydac 218TP (10 micron) C-18 column (The Separations Group, Hesperica, Calif.) by application of a linear gradient system of 0–17% acetonitrile from 10 to 97 min,. with either TFA or HFBA as counterion at a flow rate of 1 (analytical) or 2 ml/min (semi-preparative). Pyridoxamine (Sigma Chem. Co., St. Louis, Mo.) which autofluoresces was used as an internal standard.

Figure 5A:
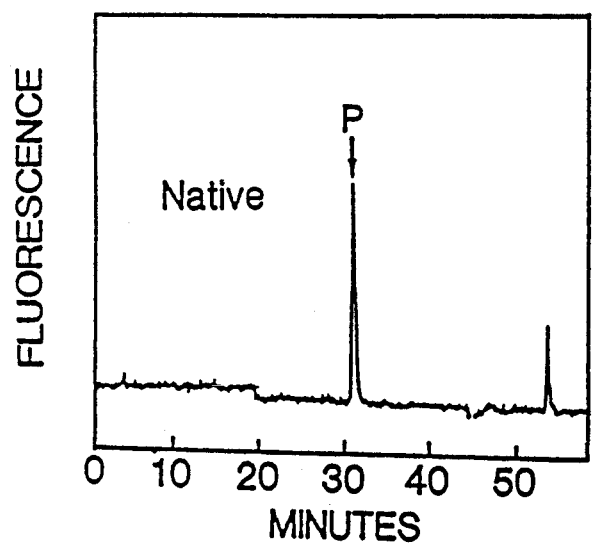
FIGS. 5A and 5B are graphs showing a comparison of a HPLC chromatogram of purified pentosidine (P) from native dura mater (FIG. 5A) to that of unpurified synthetic material (FIG. 5B). Separations were made on a 0.46×25 cm Vydac 218 TP C-18 column by application of a linear gradient of 10–17% acetonitrile in water applied from 0–35 minutes at a flow rate of 1 ml/min. with 0.01 M HFBA as the counterion. Fluorescence was monitored as of FIG. 1A.
Figure 5B:
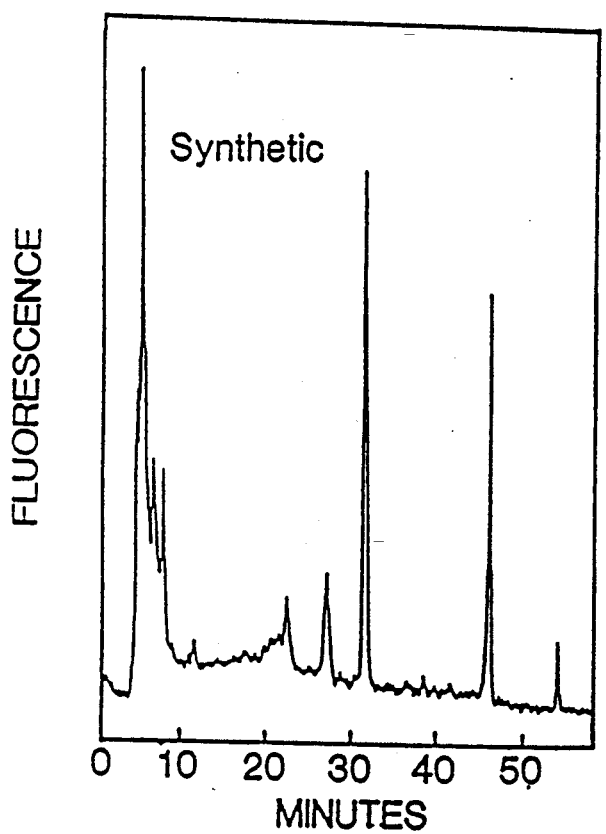
Figure 6A:
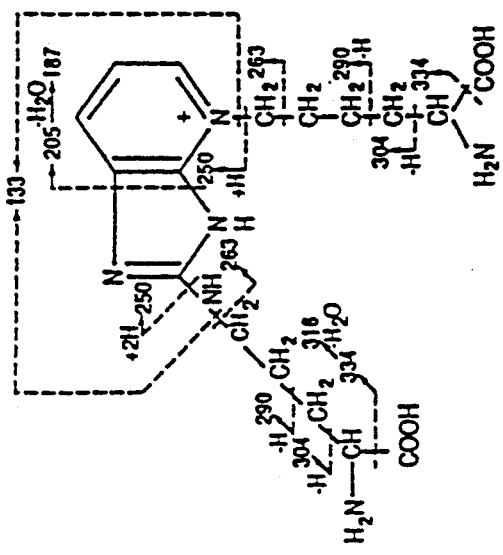
FIGS. 6A and 6B are FAB CAD MS/MS spectra of pentosidine isolated from human dura mater (FIG. 6A) and a synthetic incubation system (FIG. 6B).
Figure 6A:
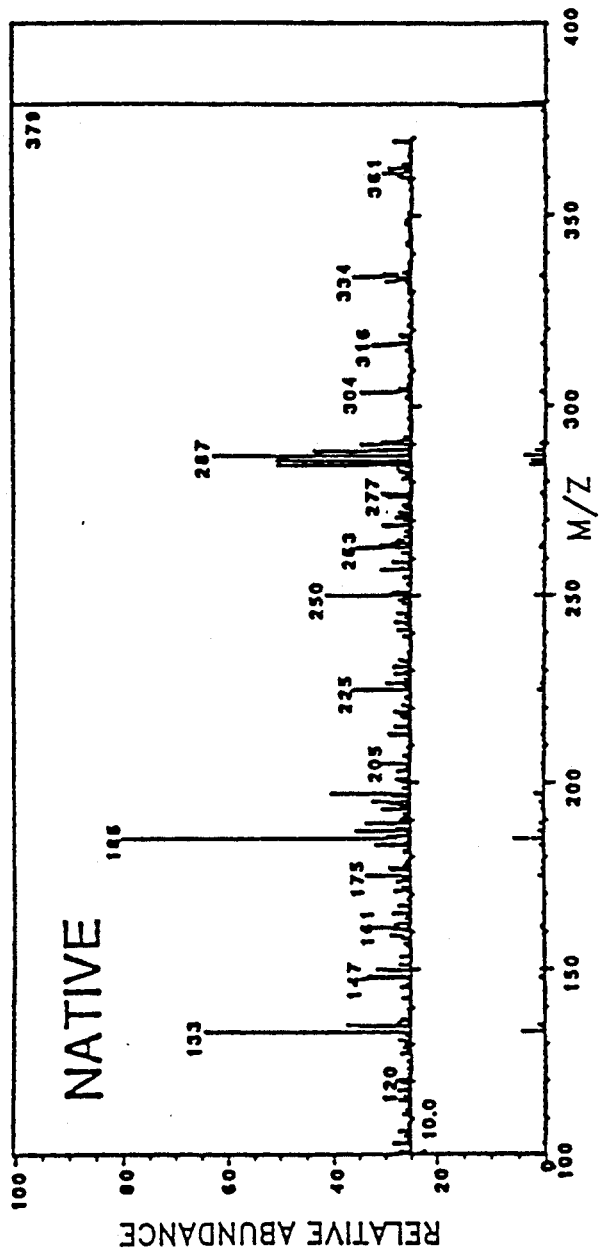
Figure 6B:
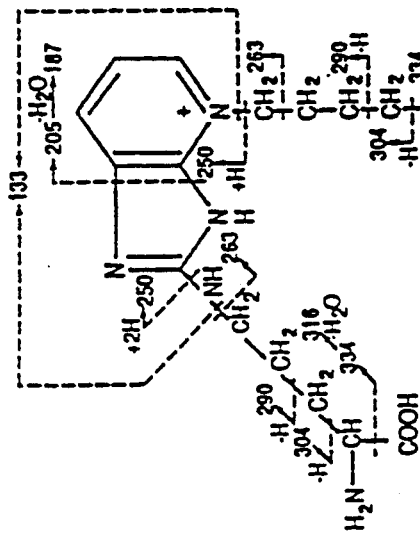
Figure 6B:
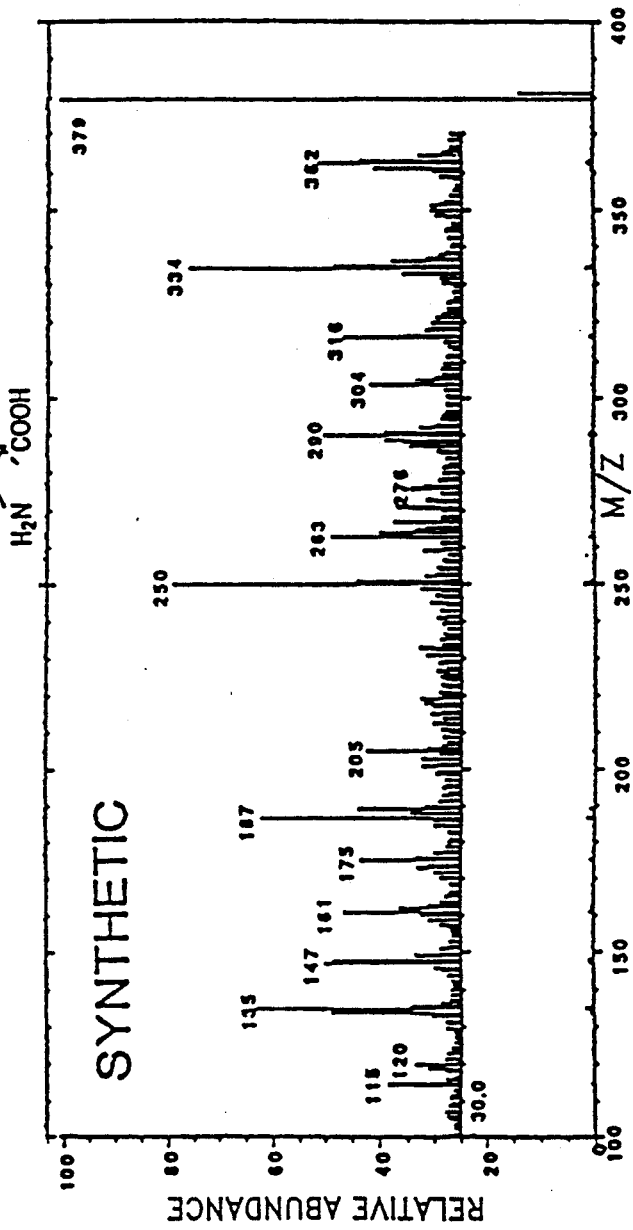

For analytical purpose, the HPLC program was shortened such that a linear gradient of 10–17% acetonitrile was applied from 0–35 min. with HFBA as the counterion (see FIG. 5).

Incubation of Sugars with L-lysine and L-arginine In Vitro

Sugars were incubated with L-lysine and L-arginine at 80° C. for 1 hour in PBS. Each sugar and amino acid were present at concentrations of 100 mM in a total volume of 2 ml in 13×100 mm test tubes placed in a Reacti-Therm heating block (Pierce Chem. Co., Rockford, Ill.

In Vitro Incubation of Young Collagen with Pentoses

A pool of young dura mater (average age 15 years) obtained at autopsy was homogenized in PBS and extracted for 24 hours in 2:1 chloroform/methanol. Dry blotted tissue (0.5 g wet weight) was incubated with 100 mM each of the pentose sugars, L-arginine and L-lysine in 12 ml of PBS containing 10 μl each of toluene and chloroform. After incubation at 37° C. for 6 days, 0.3 g wet tissue weight was withdrawn from each tube and washed three times with 5 ml portions of PBS and water, respectively. Samples were acid-hydrolyzed in 2 ml of 6 N HCl for 24 hours. Following evaporation of the acid, the material was reconstituted in 1 ml of water. Hydroxyproline content was determined as described (Hamlin, C. R., Luschin, J. H., and Kohn, R. R., *Exp. Gerontol.* 13, pp. 415–523, 1978) and equalized among samples.

Determination of Pentosidine in Tissues

Tracheal cartilage, cortical bone (iliac crest), aorta, kidney, cardiac muscle, lung, liver, skin, dura mater and lens were obtained at autopsy from elderly subjects. Cartilage, bone and aorta were decalcified. All tissues were minced and extracted with 4–5 changes of PBS before lyophilization. Red blood cells, obtained by centrifugation of human blood, were washed three times in PBS and lyophilized. The following were gifts: purified isolated human renal glomerular basement membrane from Dr. Edward C. Carlson (University of North Dakota); human and rat-cultured glomerular mesangial cells from Dr. John R. Sedor (Case Western Reserve University, School of Medicine); and mixed human fibroblasts cultured for 14 days on rat tail tendon collagen-coated petri dishes from Dr. Irwin A. Schafer (Case Western Reserve University, Cleveland Metropolitan General Hospital). Human placental, bovine Achilles tendon and calf skin collagens were purchased from Sigma Chem. Co. (St. Louis, Mo.).

Approximately 15 mg of each sample were acid-hydrolyzed in 2 ml of 6 N HCl for 24 hours. The acid was evaporated and pentosidine was quantitated by HPLC after reconstituting samples with water.

Spectroscopy

Absorption spectra were recorded with a Hewlett-Packard (HP) 8452A diode array spectrophotometer connected to an IBM PC/AT computer (Hewlett-Packard, Inc., Avondale, Pa.; IBM Corp., Boca Raton, Fla.). Fluorescence spectra were recorded with a J4-8202 Aminco-Bowman spectrophotofluorometer (SLM. Instru., Inc., Urbana, Ill.).

Samples for proton NMR spectroscopy were exchanged three times with deuterium oxide ($D_2O$) under a nitrogen atmosphere. The sample contained in 400 $\mu l$ of 100% $D_2O$ was transferred to a 5 mm NMR tube and scanned for 10 min. in a 400 MHz spectrometer (MSL 400, Bruker Instru., Inc., Billerica, Mass.). The following conditions were used (FIG. 3): spectrometer frequency, 400.13 MHz; spectral width, 1 ppm=400.13 Hz; Hz/point=0.244; acquisition time, 2.048 s (native), 1.024. s (synthetic); number of scans, 944 (native), 400 (synthetic); temperature, 297° K; recycle delay, 5 s; pulse width, 6.65 $\mu s$ corresponding to 90°. TPS(3-(trimethylsilyl)-1-propane-sulfonic acid) was used as an internal standard. For two-dimensional H,H-correlated (COSY) spectroscopy, the sample was scanned overnight.

Mass-spectrometry analyses were performed by Dr. Douglas Gage at the NIH mass-spectrometry facility in the Department of Biochemistry, Michigan State University, East Lansing, Mich. Molecular weights were determined by fast atom bombardment (FAB) spectroscopy with a JEOL HX 110HF double focusing mass spectrometer Analysis was initially conducted at low resolution (1000) at accelerating voltage of 10 KV. Samples were dissolved in 0.1% TFA and mixed with an equal volume of glycerol. Ions were formed by FAB with a 6 KeV beam of Xe atoms. Spectra which were generated by FAB CAD MS/MS analysis (collisionally activated dissociation tandem mass spectrometry) made use of a JEOL DA-5000 data-system-generated linked scans at constant B/E. Helium was used as the collision gas in a cell located in the first field-free region and the pressure was adjusted to reduce the abundance of the parent ion by 75%. FAB high resolution mass analysis was performed at resolution 20,000 by peaking matching on the glycerol matrix ion at M/Z 369.

RESULTS

Isolation and Purification of Pentosidine from Tissue

A pool of dura mater (600 g wet weight) obtained at autopsy from elderly donors (average age 77 years) was acid-hydrolyzed and fractionated by Bio-Gel P-2 gel filtration chromatography (see FIG. 1). The bulk of the fluorescence material eluting together with salt was pooled, dried by evaporation and extracted into methanol. After evaporation and reconstituting in water, the fluorescent material was purified to homogeneity by repeated injections on reverse phase HPLC. Total fluorophore recovered was 1 mg.

Structure Elucidation of Pentosidine

The fluorophore was characterized by absorption, fluorescence, $^1$H-NMR, and mass spectroscopical properties. Its UV and fluorescence maxima (FIG. 2, top) were identical with those of the previously described unhydrolyzed fluorophore (Sell, D. R., and Monnier, V. M., Conn. Tiss. Res. 19, pp. 77-92, 1989) suggesting that no damage occurred as a consequence of hydrolysis. A peculiarity was noted in fluorescence-excitation intensities which varied with pH, being highest at pH 2 and 12, and completely quenched at pH 9 (see FIG. 2).

Crucial structural information was obtained from the $^1$H-NMR spectrum (see FIG. 3, top; also FIG. 4) which showed two doublets, a and b at 7.78 and 7.94 ppm, respectively, that were coupled with the triplet c at 7.22 ppm (FIG. 4) as revealed by a COSY experiment (not shown). This configuration suggested the presence of three aromatic protons in a pyridinium molecule with substitutions in positions 5 and 6. The two uncoupled triplets at 3.9 and 3.95 ppm suggested the presence of two $\alpha$-protons compatible with the presence of two amino acids. Two other triplets (d and e in FIG. 3) were observed at 3.6 and 4.6, both coupled with aliphatic protons at 2.0 ppm. By comparison with published spectra of pyridinoline (Fujimoto, D., Moriguchi, T., Ishida, T., and Hayashi, H., Biochem. Biophys. Res. Commun. 84, pp. 52-57, 1978) (Deyl, Z., Macek, K., Adam, M., and Vancikova, Biochem. Biophys. Acta. 625, pp. 248-254, 1980) (Ogawa, T., Tsuda, T. O. M., and Kawonishi, Y., Biochem. Biophys. Res. Commun., 107, pp. 1252-1257, 1982), lysine emerged as a likely component of the fluorescent molecule.

FAB high resolution mass spectrometry showed a M/Z of 379.2069 compatible with the empirical formula $C_{17}H_{27}N_6O_4$. Taken together, the data suggested the possible presence of an imidazo [4,5b] pyridinium ring comprising a five-carbon moiety (highlighted as bold lines in the structure below) with a lysine and arginine side chain. This configuration suggested that crosslinking of the two amino acids might have occurred as a consequence of Maillard reaction with a pentose.

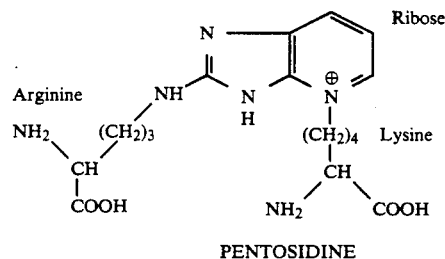

PENTOSIDINE

In Vitro Synthesis of Pentosidine

In order to confirm the pentose-derived nature of the native fluorophore 100 mM each of L-lysine, L-arginine and D-ribose were heated for 1 hour at 80° C. Injection of a small amount of this synthetic material on HPLC revealed a major fluorescent peak co-eluting with the native fluorophore. (see FIG. 5) In order to substantiate the proposed structure, the synthetic fluorophore was prepared preparatively and purified. Total yield was 21 mg; i.e., 0.02% of the reactants.

Spectroscopical Comparison of Native and Synthetic Pentosidine

The synthetic fluorophore showed the same UV and fluorescence spectra, including pH effects, as those of the native fluorophore (FIG. 2, bottom). The molar absorption coefficients of the native and synthetic compounds were determined to be 4522 and 4195 in 0.1 N. HCl, respectively.

Figure 3A:
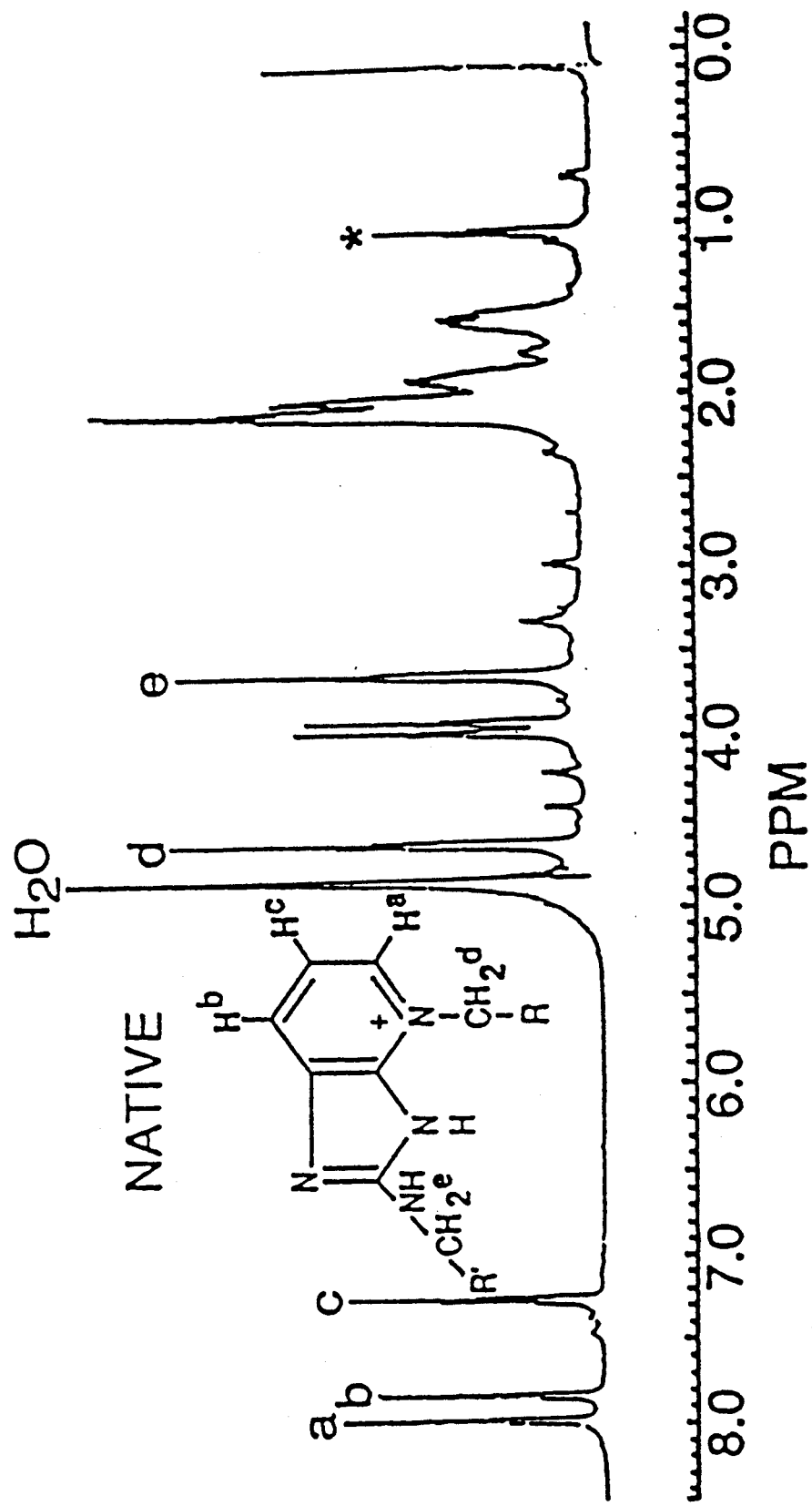
FIGS. 3A and 3B are $^1$H-NMR spectra of pentosidine isolated from human dura mater (FIG. 3A) and a synthetic incubation system (FIG. 3B).
Figure 3B:
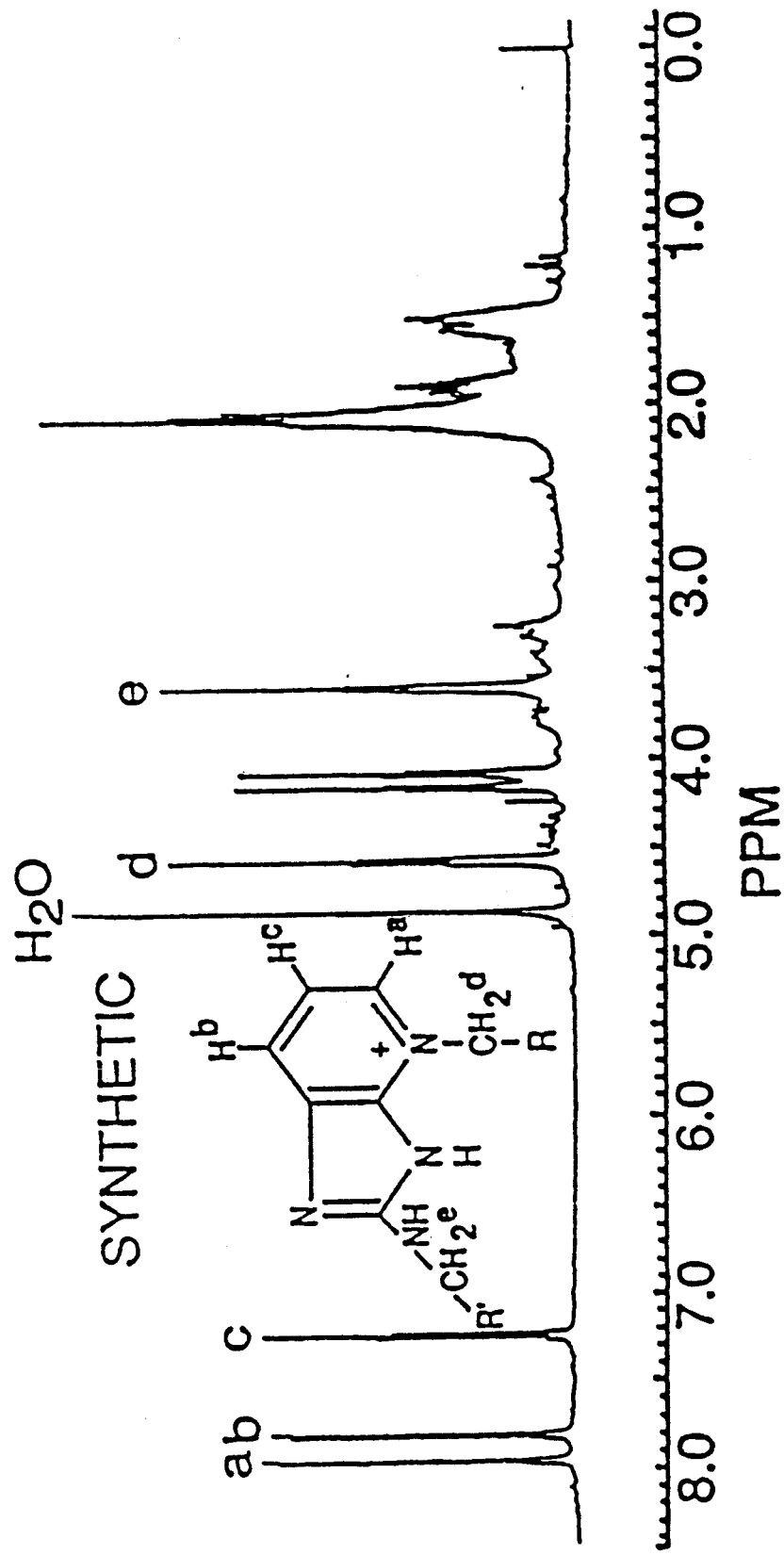
Figure 4:
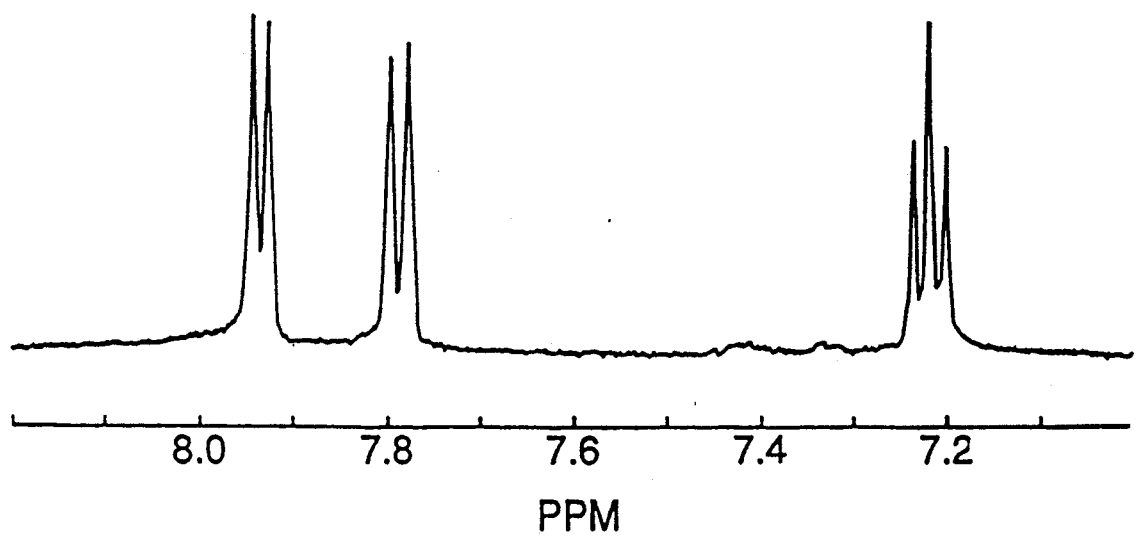
FIG. 4 is a expanded 7.1–8.2 portion of the $^1$H-NMR spectrum from FIG. 3A (native).

$^1$H-NMR spectra of the synthetic and native fluorophores were similar except for a small shift of the $\alpha$-proton triplets at 4.08 and 4.16 ppm attributable to a pH or concentration effect (FIG. 3). Other structural assignments are shown in FIG. 3.

Fragmentation patterns (FIG. 6) of synthetic and native compounds obtained by FAB CAD MS/MS analysis were also identical except for minor differences in peak intensities attributed to differences in operating conditions of the instrument since analyses were made 6 months apart. FAB high resolution analyses showed measured M/Z of 379.2069 and 379.2091 for the native and synthesized fluorophores, respectively (±0.4 ppm instrument error). The calculated mass of the proposed compound is 379.4392.

Origin of the Imidazo [4,5b] Pyridinium Ring

The spectroscopical data from the native and synthetic fluorescent molecules leaves little doubt as to the nature and structure of the newly discovered crosslink. The complete aromatization of ribose in the formation of the pyridinium ring, however, suggests that the isomers of ribose; i.e., arabinose, xylose and lyxose, can also mediate the same reaction. To test for this possibility, and to investigate the structure requirements of reducing sugars for the formation of the fluorescent molecule, hexoses and pentoses were reacted with equimolar amounts of L-lysine and L-arginine at 80° C. for 1 hour. The results are set forth below in Table I.

TABLE I

The Effects of Incubation of Various Sugars with Lysine and/or Arginine for 1 Hour at 80° C. on the Formation of Pentosidine
(Quantitated according to the conditions of FIG. 5)

| Sugar (100 mM) | L-Lysine (100 mM) | L-arginine (100 mM) | Pentosidine (nmole/ml) |
|---|---|---|---|
| D-Galactose | + | + | ND |
| D-Glucosamine | + | + | ND |
| D-Glucose | + | + | ND |
| D-Fructose | + | + | ND |
| D-Fucose | + | + | ND |
| 2-Deoxy-D-Ribose | + | + | <0.1 |
| D-Ribose-5-Phosphate | + | + | <0.1 |
| D-Ribulose | + | + | <0.1 |
| D-Xylulose | + | + | <0.1 |
| D-Xylose | + | + | 2.9 |
| D-Arabinose | + | + | 4.4 |
| D-Lyxose | + | + | 3.0 |
| D-Ribose | + | + | 5.2 |
| D-Ribose | + | − | ND |
| D-Ribose | − | + | ND |

(+) added,
(−) not added,
(ND) not detected.

Figure 7:
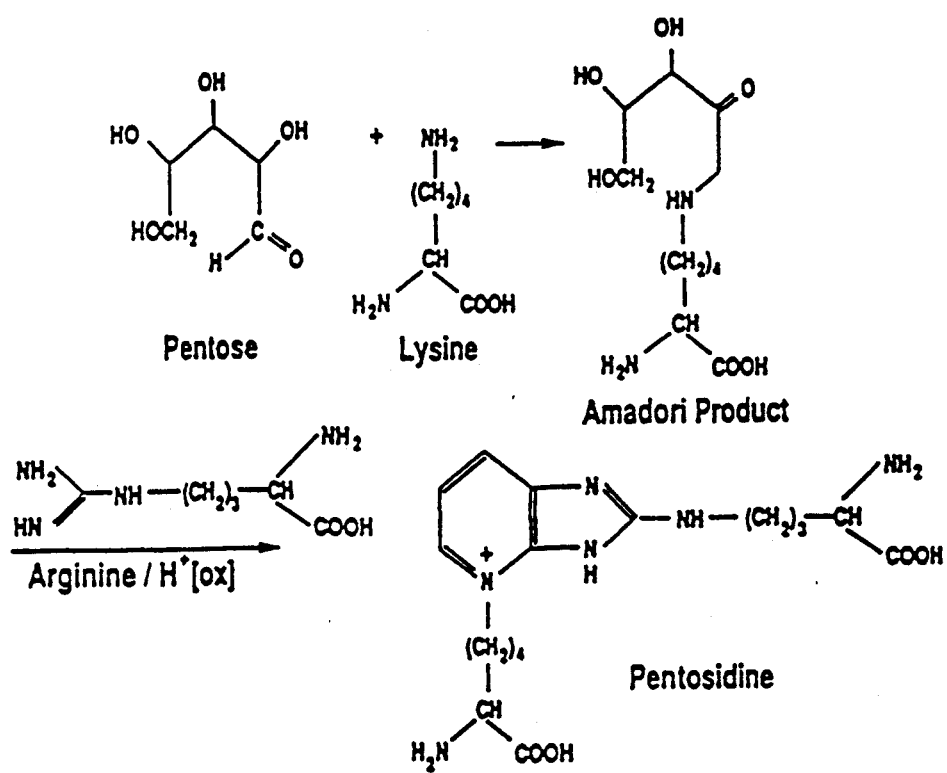
FIG. 7 is a chart indicating the proposed mechanism for the formation of pentosidine.

The results in Table 1 indicate that all three aldopentoses (xylose, arabinose and lyxose) could serve as precursors of the imidazo [4,5b] pyridinium ring. This observation led the present inventors to name the fluorophore "pentosidine". None of the hexoses tested, however, were able to generate this compound. Extremely low levels were detected with 2-deoxy-D-ribose, ribose-5-phosphate and pentuloses suggesting that commercial preparations of these sugars contain small amounts of pentosidine precursors. Pentosidine could also be synthesized by direct incubation at physiological pH and temperature of young collagen with pentoses (Table II). The highest yield was obtained with D-ribose. The addition of free lysine or arginine blocked impart the synthesis of pentosidine presumably by trapping of free ribose or intermediates of the Maillard reaction that might be involved in pentosidine synthesis (Table II, Experiment 1). A possible biosynthetic mechanism for pentosidine formation is depicted in FIG. 7.

TABLE II

The Effects of Incubation of Young Collagen With Pentose Sugars, Lysine, and/or Arginine for 6 Days at 37° C. on the Formation of Pentosidine[a]
(Quantitated according to the conditions of FIG. 5)

| Pentose (100 mM) | L-Lysine (100 mM) | L-Arginine (100 mM) | Pentosidine (pmole/mg Collagen) |
|---|---|---|---|
| \multicolumn{4}{c}{Experiment 1} | | | |
| None | − | − | 57 |
| D-Ribose | − | − | 326 |
| D-Ribose | + | − | 131 |
| D-Ribose | − | + | 118 |
| D-Ribose | + | + | 107 |
| None | + | + | 69 |
| \multicolumn{4}{c}{Experiment 2} | | | |
| None | − | − | 46 |
| D-Xylose | − | − | 125 |
| D-Arabinose | − | − | 109 |
| D-Ribose | − | − | 288 |
| D-Lyxose | − | − | 168 |

(−) no added,
(+) added

Pentosidine in Various Biological Specimens

Figure 8:
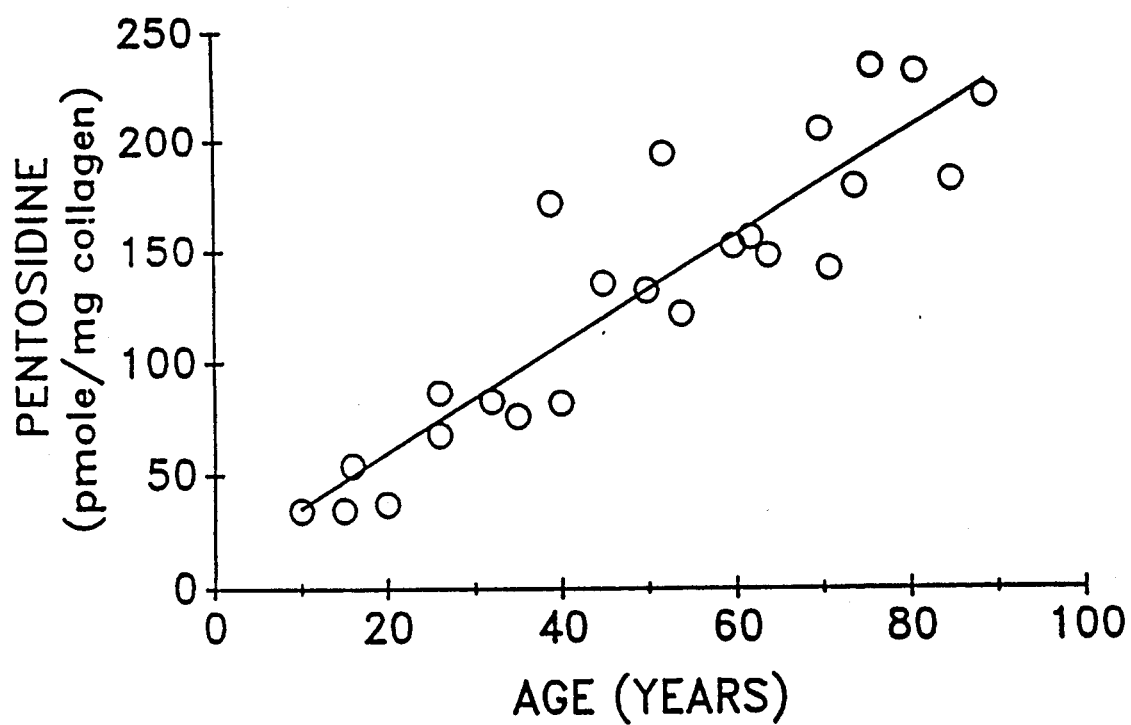
FIG. 8 is a graph showing the relationship of the pentosidine level as a function of age in human dura mater. The assay was conducted according to conditions of FIG. 5A. Line equation: pentosidine (pmol/mg collagen)=10.8+2.43 (age). N=24, p<0.001, r=91.

The presence of pentosidine was studied in a variety of tissues by HPLC. Quantitation in aging human dura mater revealed a linear 10-fold increase throughout life which reached approximately 250 pmol/mg collagen in late life (see FIG. 8). In a separate study on pentosidine level in human skin, the progression was exponential in late life but reached only 75 pmol/mg collagen suggesting a higher turnover of skin than dura mater. Pentosidine was also detected in crude preparations of human heart, aorta, lungs, cartilage, bone, tendon, liver, renal cortex and medulla, and a pure preparation of glomerular basement membrane obtained after proteolytic digestion (see Table III below). The question of whether pentosidine in these tissues originated primarily from cellular or extracellular matrix was not investigated at this point. However, pentosidine was also detected in red blood cell and plasma proteins (Table III) suggesting that the ability of pentoses to crosslink proteins is not limited to the extracellular matrix. No pentosidine was detected in commercial preparations of Type I, III, IV and V soluble collagens, but a small level was detected in a commercial preparation of insoluble Type I collagen obtained from bovine tendon (Table III).

TABLE III

Summary of Pentosidine Levels in Different Tissues
(Quantitated according to the conditions of FIG. 5)

| Tissue | pmole Collagen (mg) | Tissue (mg) |
|---|---|---|
| HUMAN: | | |
| Dura Mater | 151 | 117 |
| Skin | 29 | 27 |
| Tracheal Cartilage | 182 | 142 |
| Cortical Bone | 49 | 9 |
| Aorta | 72 | 33 |
| Cardiac Muscle | 139 | 29 |
| Lung | 116 | 29 |
| Liver | 330 | 12 |
| Kidney Cortex | 42 | 17 |
| Kidney Medulla | 63 | 25 |
| Purified Isolated Glomerular Basement Membrane | 35 | 21 |
| Red Blood Cells | — | 10 |
| Blood Proteins | — | 8 |
| Lens | — | 0.7 |
| Placenta (Commercial Types III, IV, V Soluble Collagens) | ND[a] | ND |

TABLE III-continued

Summary of Pentosidine Levels in Different Tissues
(Quantitated according to the conditions of FIG. 5)

| Tissue | pmole Collagen (mg) | Tissue (mg) |
|---|---|---|
| OTHER: | | |
| Calf Skin (Commercial Type I Soluble Collagen) | ND | ND |
| Bovine Tendon (Commercial Type I Insoluble Collagen) | 10 | 7 |
| CELL CULTURE: | | |
| Human Fibroblasts[b] | 345 | — |
| Collagen Matrix (Blank)[c] | 25 | — |

[a]ND, not detected
[b]Mixed fibroblasts cultured for 14 days on rat tail tendon collagen-coated petri dishes
[c]Represents a control consisting of collagen-coated petri dishes containing medium incubated for 14 days without cells.

A very low level was detected in the human ocular lens, a tissue with a metabolism significantly different from that of tissues rich in nucleated cells. Finally, and unexpectedly, pentosidine was detected in human fibroblasts grown in culture (Table III). A high quantity was also detected in cultures of human glomerular mesangial cells grown in a pentose-free medium. However, additional studies will be needed to determine its origin.

DISCUSSION

The discovery of an age-related accumulation of pentosidine in human extracellular matrix is the first molecular evidence for the involvement of reducing sugars in protein crosslinking. In preliminary studies, Kohn, et al. (Kohn, R. R., Cerami, A., and Monnier, V. M., *Diabetes* 33, pp. 57–59, 1984) demonstrated that rat tail tendons incubated with reducing sugars became rapidly crosslinked. The crosslinking rate as measured by tail tendon breaking time in urea was much greater for ribose than glucose and was accompanied by formation of collagen-linked fluorescence. While the study which resulted in the present invention was in progress, Tanaka, et al. (Tanaka, S., Avigad, G., Eikenberry, E. F., and Brodsky, B., *J. Biol. Chem.*, 263 pp. 17650–17657, 1988) reported the isolation of highly fluorescent dimers of α chains crosslinked in triple-helical regions of ribose-incubated rat tail tendon collagen.

Although these studies suggested that the pentose could mediate crosslinking in vitro, the discovery of pentose-mediated crosslinking in vivo is quite unexpected and raises a number of biochemical and biological questions concerning the origin and role of pentosidine. The absence of detectable pentosidine in solutions of glucose incubated for 1 hour at 80° C. with equimolar lysine and arginine suggests that glucose and its Amadori product are unlikely precursors of pentosidine. However, little browning was yet detectable after 60 min. and a fragmentation of glucose or its Amadori product into a pentose upon prolonged reaction is not excluded. Similarly, studies will be needed to evaluate the possible contribution of glyco-conjugates to pentosidine recovered from acid-hydrolyzed biological specimens. In this sense, the data presented in Table III should be considered as preliminary. Albeit this word of caution, there is little doubt that pentosidine forms spontaneously in aging since it increased in an enzymatic hydrolysate of human dura mater with age (Sell, D. R., and Monnier, V. M., *Conn. Tiss. Res.* 19, pp. 77–92, 1989).

In contrast to the extensive literature on blood and tissue levels of glucose, however, only a scant amount of information is available on the source and the level of free pentoses in tissue and body fluids. All three sugars, ribose, xylose and arabinose, have been detected in the urine with excretion rates of 5, 8.5 and 14 μg/min, respectively (Bell, D. J., and Talukder, M., Q-K, *Clin. Chim. Acta.* 40, pp. 13–20, 1972). Total pentose level in human plasma has been estimated at 44 μM (McKay, E., *Clin. Chim. Acta,* 10, pp. 320–329, 1964), but no information is available on the concentration of particular pentoses.

A number of observations suggest that ribose or one of its metabolites is a likely precursor of pentosidine in vivo. First, of all tested pentoses, ribose was the most reactive sugar in the synthesis of pentosidine (Table II). This observation is in agreement with previous determinations of the chemical reactivity of ribose (Overend, W. G., Peacoke, A. R., and Smith, J. B., *J. Chem. Soc.,* pp. 3487–3492, 1961). Second, free arabinose and xylose are thought to arise primarily from alimentary sources, mainly through the ingestion of fruits and the bacterial degradation of xylans in the intestine (McKay, E., *Clin. Chim. Acta,* 10, pp. 320–329, 1964) (Date, J. W., Scand. J. Clin. Lab. Invest., 10, pp. 155–162, 1958). Thus, it is unlikely that these sugars would explain pentosidine formation in cell culture. Third, lyxose has been only associated with heart muscle (Pailares, E. S., and Garza, H. M., *Arch. Biochem.*, 22, pp. 63–65, 1949). Finally, the detection of high pentosidine levels in cell culture (Table III) is strongly suggestive for leakage or release of significant amounts of free ribose or its metabolites as a consequence of accelerated ribonucleotide turnover, cellular turnover or cell death. In this regard, a possible source for a precursor of pentosidine could come from ADP-ribosylation reactions which play a crucial role in many cellular functions, including DNA repair mechanisms which are thought to play a role in cellular aging (Ueda, K., and Hayaisha, O., *Ann. Rev. Biochem.* 54, pp. 73–100, 1985). Yet, these propositions are speculations that will need to be addressed experimentally.

Pentosidine is of significance for gerontological research for two reasons. First, pentosidine may contribute to the age-related stiffening of tissues by crosslinking of the extracellular matrix. The extent of crosslinking can be estimated by the relative amount of crosslinks found in old human dura mater collagen assuming a molecular weight of 300,000 for the triple-helical region. The presence of 250 pmol/mg collagen translates into 7.5% modification (0.075 mol/mol of collagen). This would be compatible with a 2 to 3-fold decrease in collagen digestibility according to the estimate by Vater, et al. (Vater, C. A., Harris, E. D., and Siegel, R. C., *Biochem. J.,* 1881, pp. 639–645, 1979). It is also possible that additional pentose derived crosslinks would form during aging because pentosidine was only one of many compounds present in the reaction mixture of arginine, lysine and ribose. Second, pentosidine may serve as a molecular marker of the aging process and its availability should greatly facilitate studies on longevity and the potential role of Maillard-mediated damage by pentoses in the life-span limiting process.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A substantially pure form of imidazo [4,5b] pyridinium consisting essentially of a lysine and an arginine residue crosslinked by a pentose.

2. A substantially pure form of imidazo [4,5b] pyridinium having the configuration of:

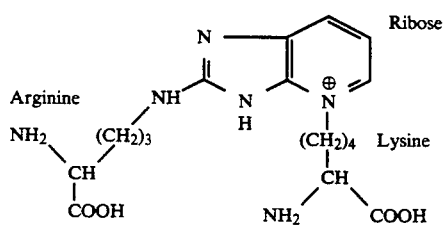

and having a U.V. maxima at 325 nm and an excitation/fluorescence maxima at 335/385 nm.

3. A substantially pure form of 3-H-imidazol [4,5b] pyridine-4 hexanoic acid, alpha amino-2 [(4-amino-4-carboxybutyl)amino] having a U.V. maxima at 325 nm and an excitation/fluorescence maxima at 335/385 nm.

4. The imidazo [4,5b] pyridinium of claim 1, wherein the imidazo [4,5b] pyridinium was isolated from human collagen undergoing advanced non-enzymatic glycosylation.

5. The imidazo [4,5b] pyridinium of claim 2, wherein said compound was isolated from human collagen undergoing advanced non-enzymatic glycosylation.

6. The imidazo [4,5b] pyridinium of claim 1, wherein said imidazo [4,5b] pyridinium is 2-alkylamino-4-alkyl imidazo [4,5b] pyridinium having a U.V. maxima at 325 nm and an excitation/fluorescence maxima at 335/385 nm.

7. An isolated peptide-linked fluorophore obtained by a process comprising the steps of:
   a) providing insoluble collagen;
   b) cleaving the high molecular weight tryptic peptides of the insoluble collagen by sequential enzymatic digestion;
   c) separating the high molecular weight and low molecular weight peptide fractions by gel filtration chromatography;
   d) recovering the low molecular weight fractions and further separating the low molecular weight peptide fractions by paper and reverse phase chromatography (HPLC);
   e) exciting the separated low molecular weight peptide fractions with UV light and obtaining the peptide-linked fluorophore having a UV maxima at 325 nm and excitation/fluorescence maxima at 335/385 nm.

8. A peptide-linked fluorophore structurally elucidated by a process comprising the steps of:
   a) providing insoluble collagen;
   b) cleaving the high molecular weight tryptic peptides of the insoluble collagen by sequential enzymatic digestion;
   c) separating the high molecular weight and low molecular weight peptide fractions by gel filtration chromatography;
   d) recovering the low molecular weight fractions and further separating the low molecular weight peptide fractions by paper and reverse phase chromatography (HPLC);
   e) exciting the separated low molecular weight peptide fractions with UV light and obtaining the peptide-linked fluorophore having a UV maxima at 325 nm and excitation/fluorescence maxima at 335/385 nm; and
   f) conducting $^1$H-NMR, $^{13}$C-NMR, and MS/MS fast atom bombardment spectroscopy in order to elucidate the structure of the peptide-linked fluorophore.

9. A 335/385 nm fluorophore prepared by a process comprising the steps of:
   a) acid hydrolysing insoluble dura mater collagen;
   b) evaporating the acid and dissolving the residue in water;
   c) fractionalizing the water-residue mixture by Bio-Gel P-2 gel filtration chromatography;
   d) collecting the fractions containing the 335/385 nm fluorophore; and,
   e) purifying the collected fractions containing the 335/325 nm fluorophore by multiple injections/peak collections using a reverse-phase C-18 HPLC.

10. An imidazo [4,5b] pyridinium fluorophore characterized by a process comprising the steps of:
    a) providing insoluble collagen;
    b) cleaving the high molecular weight tryptic peptides of the insoluble collagen by sequential enzymatic digestion;
    c) separating the high molecular weight and low molecular weight peptide fractions by gel filtration chromatography;
    d) recovering the low molecular weight fractions and further separating the low molecular weight peptide fractions by paper and reverse phase chromatography (HPLC);
    e) exciting the separated low molecular weight peptide fractions with UV light and obtaining the peptide-linked fluorophore having a UV maxima at 325 nm and excitation/fluorescence maxima at 335/385 nm; and
    f) characterizing the fluorophore by absorption, fluorescence, $^1$H-NMR, and mass spectroscopical properties.

11. An imidazo pyridinium compound synthesized by a process comprising the steps of:
    a) heating a mixture containing D-ribose, L-lysine and L-arginine to a temperature of about 80° C. for about 60 minutes;
    b) cooling the mixture;
    c) passing the cooled mixture over a Dowex 50×4-400 ion-exchange resin;
    d) washing the resin with water and 1M pyridine followed by elution of the imidazo pyridinium containing material with NaOH;
    e) neutralizing the eluted imidazo pyridinium-material with an acid;
    f) concentrating the neutralized imidazo-pyridinium material by evaporation;
    g) purifying the concentrated imidazo-pyridinium material by passing the material through a Bio-Gel P-2column; and,
    h) further purifying the fractions containing the imidazo-pyridinium compound by HPLC using a C-18 reverse phase column and a linear gradient of acetonitrile with heptafluorobutyric acid as the counter ion.

12. The imidazo pyridinium compound chemically synthesized by a process comprising the steps of:
 a) heating a mixture containing D-ribose, L-lysine, and L-arginine at a pH of about 7.4 to a temperature about 80° C. for about 60 minutes;
 b) passing the mixture over a Dowex 50×4 resin (H+form);
 c) washing the resin with water and pyridine; and,
 d) eluting the imidazo pyridium compound from the resin with NaOH.

13. An imidazo pyridinium compound synthesized by a process comprising the steps of:
 a) non-enzymatically reacting D-ribose, L-lysine and L-arginine to form a glycosylated peptide mixture;
 b) passing the glycosylated peptide mixture over a Dowex 50 ×4 resin (H+form);
 c) washing the resin with water and pyridine; and,
 d) eluting the imidazo pyridium compound from the resin with NaOH.

* * * * *